United States Patent
Noyce et al.

(10) Patent No.: US 10,408,794 B2
(45) Date of Patent: Sep. 10, 2019

(54) POROUS RESONANT SENSORS

(71) Applicant: BRIGHAM YOUNG UNIVERSITY, Provo, UT (US)

(72) Inventors: Steven Noyce, Provo, UT (US); Robert C. Davis, Provo, UT (US); Richard R. Vanfleet, Provo, UT (US)

(73) Assignee: Brigham Young University (BYU), Provo, UT (US)

( * ) Notice: Subject to any disclaimer, the term of this patent is extended or adjusted under 35 U.S.C. 154(b) by 0 days.

(21) Appl. No.: 14/929,237

(22) Filed: Oct. 30, 2015

(65) Prior Publication Data
US 2016/0123930 A1 May 5, 2016

Related U.S. Application Data

(60) Provisional application No. 62/122,778, filed on Oct. 30, 2014.

(51) Int. Cl.
*G01N 29/02* (2006.01)
*G01N 29/24* (2006.01)
*G01N 29/036* (2006.01)

(52) U.S. Cl.
CPC ......... *G01N 29/022* (2013.01); *G01N 29/036* (2013.01); *G01N 29/2437* (2013.01); *G01N 2291/021* (2013.01); *G01N 2291/022* (2013.01); *G01N 2291/0255* (2013.01); *G01N 2291/0256* (2013.01); *G01N 2291/0427* (2013.01)

(58) Field of Classification Search
None
See application file for complete search history.

(56) References Cited

U.S. PATENT DOCUMENTS

2011/0212535 A1* 9/2011 Kaul ............... B82Y 30/00
436/149

OTHER PUBLICATIONS

Mancuso et al., Nanoporous polymer ring resonators for biosensing, Optics Express, vol. 20, No. 1, pp. 245-255, 2 Jan. 2, 2012.*
Ong et al., Fluorescent Gas Sensors Based on Nanoporous Optical Resonators (Microcavities) Infiltrated with Sensory Emissive Polymers, IEEE Sensors Journal, vol. 11, No. 11, Nov. 2011, pp. 2947-2951.*
Park et al., Multimodal label-free detection and discrimination for small molecules using a nanoporous resonator, Nature Communications, 5:3456, Mar. 28, 2014, pp. 1-8.*
Battiston, et al., "A chemical sensor based on a microfabricated cantilever array with simultaneous resonance-frequency and bending readout", Chemical Sensors and Actuators B, 2001, 122-131.
(Continued)

*Primary Examiner* — Rebecca L Martinez
(74) *Attorney, Agent, or Firm* — Brake Hughes Bellermann LLP

(57) ABSTRACT

In a general aspect, an apparatus can include a porous, monolithic resonator having nanoscale pores defined therein. The apparatus can also include an adsorbent selective to a given analyte disposed on an exterior of the porous, monolithic resonator, the exterior of the porous, monolithic resonator including surfaces defining the nanoscale pores.

17 Claims, 10 Drawing Sheets

(56) References Cited

OTHER PUBLICATIONS

Blom, et al., "Dependence of the quality factor of micromachined silicon beam resonators on pressure and geometry", Journal of Vacuum Science & Technology B: Microelectronics and Nanometer Structures, 1992, 19-26.

Candler, et al., "Impact of Geometry on Thermoelastic Dissipation in Micromechanical Resonant Beams", Journal of Microelectromechanical Systems, 2006, 927-934.

Hutchison, et al., "Carbon nanotubes as a framework for high-aspect-ratio MEMS fabrication", Journal of Microelectromechanical Systems, 2010, 75-82.

Hwang, et al., "Porous Silicon Resonators for Improved Vapor Detection", Journal of Microelectromechanical Systems, 2012, 235-242.

Tamayo, et al., "Chemical sensors and biosensors in liquid environment based on microcantilevers with amplified quality factor", Ultra Microscopy, 2001, 167-173.

Van Eysden, et al., "Resonant frequencies of a rectangular cantilever beam immersed in a fluid", Journal of Applied Physics, 2006, 114916-1 to 114916-8.

Waggoner, et al., "Micro-and nanomechanical sensors for environmental, chemical, and biological detection", Lab on a Chip, 2007, 1238-1255.

\* cited by examiner

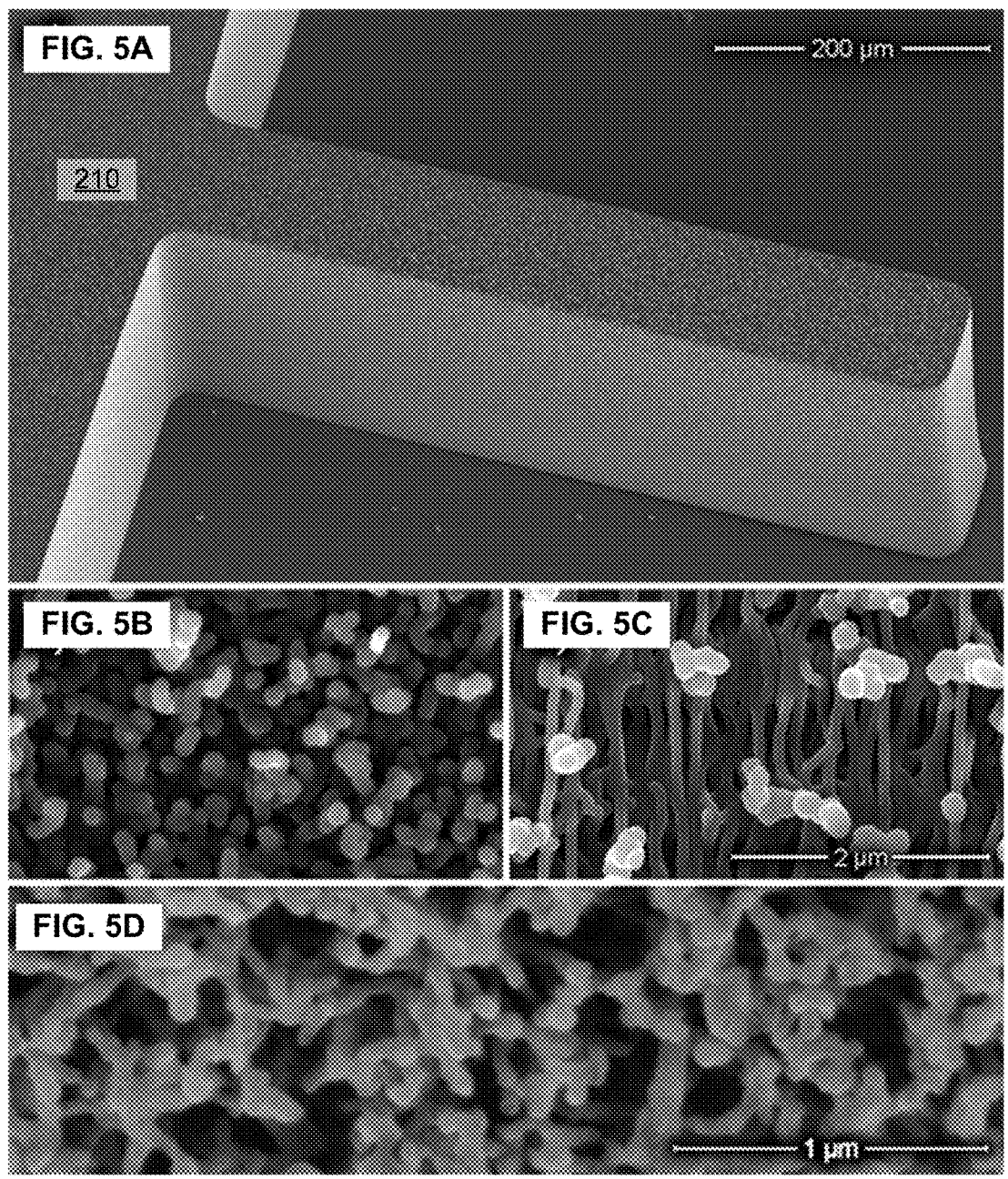

POROUS RESONANT SENSORS

RELATED APPLICATIONS

This application claims priority to and the benefit of U.S. Provisional Patent Application No. 62/122,778, filed Oct. 30, 2014, which is incorporated herein by reference in its entirety.

TECHNICAL FIELD

This description relates to resonant sensors. More specifically, the description relates to porous, monolithic resonant sensors that can be used for chemical and/or biological sensing.

BACKGROUND

Micro-scale resonators (e.g., micro-cantilever resonators) can be used in many applications such as chemical sensing, biological sensing, atomic force microscopy, and other measurement applications. However, a limiting factor in the precision of measurements made with such sensors is the quality factor (Q) of a given resonator. A quality factor for a resonant sensor can be determined as the resonant frequency of the resonator divided by the width of that resonant frequency peak of the resonator. Further, to obtain specificity to a desired analyte, these resonant sensors can include surface coatings that not only selectively bind the desired analyte, but also cause the desired analyte to bind in such a way that it affects (e.g., linearly affects) a property to be measured (e.g., resonant frequency).

In such resonant sensors, in order to have a mass ratio between the cantilever and an adsorbed chemical or biological analyte (e.g., bound to a surface coating) sufficient for accurate sensing, it is preferable that the resonator (sensor) be thin (e.g., have a low aspect ratio). However, in order to have a high quality factor, it is preferable that the resonator be thick (e.g. have a high aspect ratio). These opposing goals lead to making a tradeoff between a low aspect ratio and a high aspect ratio in current resonant sensor devices, such as may be determined for a desired application. Additionally, current implementations are limited in achieving mass ratios (e.g., sensor to bound analyte) that are sufficient for accurate sensing by a surface area of the sensor that is available for binding a desired analyte. The consideration can also factor into the aspect ratio tradeoff decision.

Additionally, while certain resonant sensors (e.g., micro-cantilever sensors) have demonstrated mass detection limits down to 7 zeptograms ($10^{-21}$ g) in vacuum, such mass detection sensitivities in fluid environments have not been achieved for these resonant sensors due, at least in part, to fluid damping causing low quality factors, which can result, in part, from the aspect ratio tradeoff discussed above.

SUMMARY

In one general aspect, an apparatus can include a porous, monolithic resonator having nanoscale pores defined therein. The apparatus can also include an actuator coupled with the porous, monolithic resonator. The apparatus can further include a detector operatively associated with the porous, monolithic resonator. The detector can be configured to determine a response of the resonator when the resonator is driven at or near a resonant frequency of the porous, monolithic resonator by the actuator.

Implementations can include one or more of the following features. For example, the porous, monolithic resonator can include a carbon nanotube composite structure including a patterned carbon nanotube forest and an infiltration material. At least a portion of the patterned carbon nanotube forest can have a height:width aspect ratio up to 200:1, up to 300:1 or up to 500:1. The porous, monolithic resonator can be one of a cantilever resonator, a beam resonator and a membrane resonator.

The porous, monolithic resonator can include a plurality of micro-scale pores defined therethrough, a first micro-scale pore of the plurality of micro-scale pores being substantially linear and substantially parallel to a second substantially linear micro-scale pore of the plurality of micro-scale pores. A longitudinal axis of the first micro-scale pore can be substantially perpendicular to a direction of vibration of the porous, monolithic resonator. A longitudinal axis of the first micro-scale pore can be substantially parallel to a direction of vibration of the porous, monolithic resonator.

The apparatus can include an adsorbent that is selective to a corresponding analyte, the adsorbent being disposed on an exterior of the porous, monolithic resonator. A resonant frequency of the porous, monolithic resonator can be dependent on an amount of the corresponding analyte adsorbed by the adsorbent. The exterior of the porous, monolithic resonator can include surfaces defining the nanoscale pores. The adsorbent can be one of a protein, an antibody and a polymer.

In another general aspect, a method can include defining a porous, monolithic resonator having nanoscale pores defined therein. The method can also include depositing an adsorbent that is selective to a corresponding analyte on an exterior of the porous, monolithic resonator. The exterior of the porous, monolithic resonator can include surfaces defining the nanoscale pores.

Implementations can include one or more of the following features. For example, the method can include coupling the porous, monolithic resonator with an actuator; exposing at least a portion of the porous, monolithic resonator to the corresponding analyte; energizing the porous, monolithic resonator with the actuator at or around a resonant frequency of the porous, monolithic resonator; determining a response of the porous, monolithic resonator to the energizing, the response being one of a phase shift, and an amplitude change and a change in the resonant frequency; and determining, based on the response, an amount of the analyte adsorbed by the adsorbent.

The resonant frequency can be a first resonant frequency. The method can include, prior to exposing the at least a portion of the porous, monolithic resonator to the corresponding analyte: energizing the porous, monolithic resonator with the actuator; determining a second resonant frequency of the porous, monolithic resonator; and de-energizing the porous, monolithic resonator. The determining the amount of the analyte adsorbed by the adsorbent can be based on a difference between the second resonant frequency and the first resonant frequency.

The exposing the at least a portion of the porous, monolithic resonator to the corresponding analyte can include exposing the at least a portion of the porous, monolithic resonator to the corresponding analyte in a gas phase. The exposing the at least a portion of the porous, monolithic resonator to the corresponding analyte can include exposing the at least a portion of the porous, monolithic resonator to the corresponding analyte in a liquid phase.

In another general aspect, an apparatus can include a porous, monolithic resonator having nanoscale pores defined therein. The apparatus can also include an adsorbent selective to a given analyte disposed on an exterior of the porous, monolithic resonator. The exterior of the porous, monolithic resonator can include surfaces defining the nanoscale pores.

Implementations can include one or more of the following features. For example, the porous, monolithic resonator can have a quality factor of at least 100 in a gas environment. The porous, monolithic resonator can have a quality factor of at least 10 in an aqueous environment. The adsorbent can be one of a protein, an antibody and a polymer. The adsorbent can be a porous polymer configured to adsorb at least one of a volatile and a semi-volatile chemical compound. The porous, monolithic resonator can include a patterned carbon nanotube structure including a carbon nanotube forest infiltrated with an infiltration material.

The details of one or more implementations are set forth in the accompanying drawings and the description below. Other features will be apparent from the description and drawings, and from the claims.

BRIEF DESCRIPTION OF THE DRAWINGS

FIGS. 5A through 5D are images illustrating microstructure and/or nanostructure of a porous, monolithic resonant sensor, according to an implementation.

DETAILED DESCRIPTION

Figure 1:
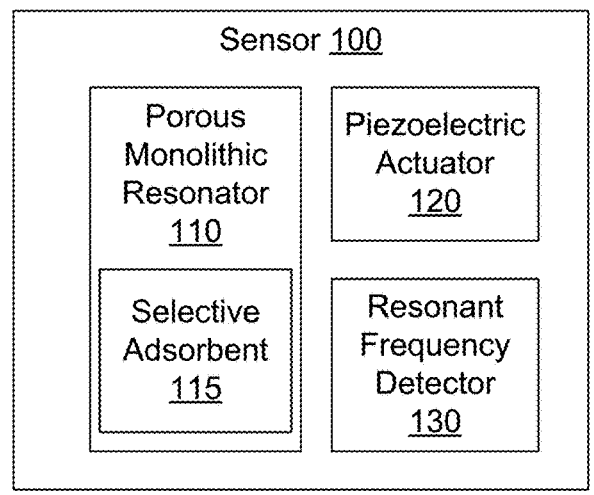
FIG. 1 is a diagram that illustrates an example of a sensor apparatus that can be used for sensing/detecting the presence and/or concentration of a chemical and/or biological analyte, according to an implementation.

Micro-resonator sensors produced from a porous (e.g., fully porous) material can address at least some of the drawbacks of current implementations discussed above. For instance, such sensors could have a relatively low mass and a high aspect ratio (as compared with current resonant sensors produced from solid materials). Accordingly, resonant sensors produced from porous materials could obtain better mass ratios as well as improved quality factors (as compared to current implementations) that are sufficient for accurate sensing in gas and liquid environments (as well as in a vacuum). In addition, a porous (fully porous) resonant sensor could have an exposed surface area (due to surface area within the pores), on which an adsorbent can adhere, that is orders of magnitude higher than a nonporous (solid) sensor. This increase in exposed surface area can greatly increases a mass of an adsorbed chemical or biologic to be sensed (e.g., due to an associated increase in available binding surface area), while simultaneously allowing for a low cantilever mass and a beneficial (high) quality factor, as compared to current sensors. However, one difficulty with producing such porous micro-resonators is that traditional micro-fabrication processes are not compatible with porous materials that are appropriate for producing micro-resonators, or can only be used to produce low aspect ratio micro-resonators.

This disclosure describes micro-resonator sensors that are produced using a carbon nanotube template microfabrication (CNT-M) process to produce high aspect ratio, porous, monolithic (e.g., freestanding) micro-structures for use as resonant sensors. Using this CNT-M process, as described herein, porosity of these devices can be precisely controlled, as well as geometry and density of the sensor material. This disclosure also describes measurement techniques, material characterization and porosity control of such micro-resonator sensor structures.

Briefly, such porous micro-resonator sensors can provide highly sensitive concentration (analyte) detection, even in gas or liquid environments. The CNT-M fabrication process can be used to produce porous, monolithic (e.g., freestanding) resonators made from a carbon nanotube composite structure that includes a patterned carbon nanotube forest an infiltration material (e.g., that is used to partially fill interstices between carbon nanotubes of the patterned carbon nanotube forest). Infiltration materials can include ceramics, carbon, nanocrystalline carbon, amorphous carbon, silicon, silicon dioxide, silicon nitride, metals, tungsten, nickel, copper, metal oxides, alumina, hafnia, titania, polymers, poly(p-xylylene), polymethacralate as some examples.

Resulting structures can have densities that are tunable (by varying infiltration time) within in a range of $10^2$ to $10^3$ kg/m$^3$, with pore diameters on the order of hundreds of nanometers down to several nanometers (e.g., nanoscale pores). Empirical resonance measurements on porous, monolithic micro-cantilever resonators with beam lengths ranging from 100 μm to 10 mm in vacuum, air, and water, show resonant properties in each medium with quality factors on the order of $10^3$, $10^2$, and $10^1$, respectively.

In an example implementation, a fully porous microcantilever resonator with a beam length on the order of hundreds of microns can have more than three orders of magnitude more analyte binding (e.g., adsorbent) surface area than a similar solid micro-cantilever resonator. With other factors held constant, analyte detection sensitivity using such as a fully porous, monolithic micro-cantilever resonator can increase by approximately the same amount, e.g., three orders of magnitude. While such increases in detection sensitivity may not be of a significant benefit in vacuum environments, such increases can be extremely beneficial for analyte sensing in fluid (e.g., gas and aqueous) environments.

Furthermore, a fully porous micro-resonator sensor can also provide an advantage over a comparable solid micro-resonator sensor, in that a ratio of a mass of an analyte that is adsorbed to a mass of the sensor body may not vary significantly with sensor geometry. This advantage can allow for geometries of a porous sensor to be modified in ways that are not possible for solid, or even partially porous micro-resonator sensors (e.g., micro-resonator sensors having porous surface treatments). For example, increasing a thickness of a fully porous micro-resonator sensor can add energy to each vibrational mode without greatly influencing fluid damping, allowing it to exhibit a higher quality factor. This effect can be significant in implementations where fluid damping is typically dominant, as is the case in fluid environments, such as gas and liquid environments. Solid and partially porous micro-resonator sensors must be relatively thin (as compared to the fully porous sensors described herein) so that the sensor mass (in a solid or mostly solid sensor) does not overpower an adsorbed analyte mass. In comparison, the increased surface area of fully porous micro-resonator (resonator) sensors can overcome this constraint.

The carbon nanotube templated microfabrication (CNT-M) process, described herein, such as with respect to FIGS. 3A-3F, can be used to produce micro-scale features (e.g., resonators) from porous (e.g. nanoporous) materials with aspect ratios (e.g., of carbon nanotubes with the material) of up to 200:1, up to 300:1, up to 500:1, and so forth. Briefly, in an example implementation of a CNT-M process, a thin film of iron can be patterned on an alumina coated silicon substrate, where the alumina prevents diffusion of the iron into the silicon substrate during thermal processing to form a sensor structure. Carbon nanotubes (e.g., a patterned carbon nanotube forest) can then be grown from the patterned iron catalyst layer, where the carbon nanotubes of the carbon nanotube forest are perpendicular (substantially perpendicular) to the silicon substrate. After growing the carbon nanotubes, interstices between the nanotubes can be infiltrated with other materials (such as the infiltration materials described herein) to form a cohesive, freestanding, monolithic micro-resonator structure that can be chemically and or mechanically removed from the silicon substrate. As also described herein, the extent of (amount of) infiltration can be adjusted to, e.g., control the porosity of the structure (as well as the density).

Again, this disclosure is directed to high aspect ratio porous (e.g., fully porous, which can be described as being substantially uniformly porous across a structure thickness), monolithic micro-resonator sensors produced (e.g., using a CNT-M process) from a patterned carbon nanotube structure that includes a carbon nanotube forest coated with an infiltration material (e.g., nanocrystalline carbon or other appropriate nanofilm), as well as associated methods of manufacturing and using such a micro-resonator sensor.

Material characterization, including porosity control, for such micro-resonator sensors is also described. For instance, such micro-resonator sensors can be precisely micro-fabricated with tunable porosities (e.g., based on infiltration time) covering a wide porosity range, with corresponding device densities spanning an order of magnitude. Resonant characteristics of such micro-resonator sensors, as well as their responses in vacuum, air, and aqueous environments, are also described. Further, effects of thermoelastic dampening (TED) on (and associated benefits of) fully porous micro-resonator sensors in air and liquid are described.

FIG. 1 is a diagram that illustrates an example of a sensor apparatus 100 that can be used for sensing/detecting the presence and/or concentration of a chemical and/or biological analyte, according to an implementation. In this implementation, the sensor 100 includes a porous, monolithic resonator (resonator) 110, a piezoelectric actuator (actuator) 120 and a resonant frequency detector (detector) 130. Further in the implementation of FIG. 1, the resonator 110 can included a selective adsorbent 115 that is disposed on an exterior of the resonator 110, the exterior including surfaces of the resonator 110 that define pores (e.g., nanoscale pores) in the resonator 110.

In an implementation, the resonator 110 can be formed from a fully porous, patterned carbon nanotube structure (e.g., produced using a CNT-M process, such as described herein). For instance, the carbon nanotube structure of the resonator 110 can include a carbon nanotube forest that is infiltrated with nanocrystalline carbon, such that nanoscale pores (e.g., pores on the order of hundreds of nanometers) are defined in the carbon nanotube structure. In an implementation, a carbon nanotube composite structure (e.g., a patterned forest of carbon nanofilm coated nanotubes) can have geometric features, such as a beam of a micro-resonator, that have a height:width aspect ratio greater than 200:1, greater than 300:1, greater than 500:1, and so forth. The resonator 110, as some examples, can be a cantilever (e.g., micro-cantilever) resonator, a beam resonator or a membrane resonator, such as those illustrated in FIGS. 2A-2C and described herein. The resonator 110 can, of course, take other forms.

Figure 2A:
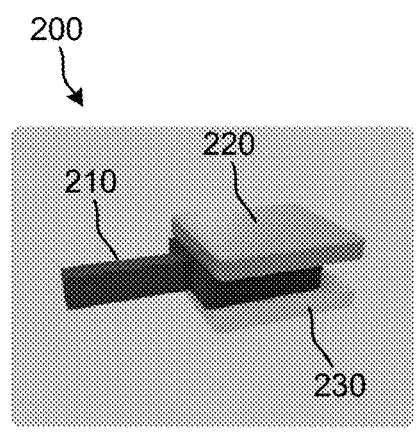
FIGS. 2A through 2C are diagrams that illustrate example resonant sensors, according to implementations.
Figure 2B:
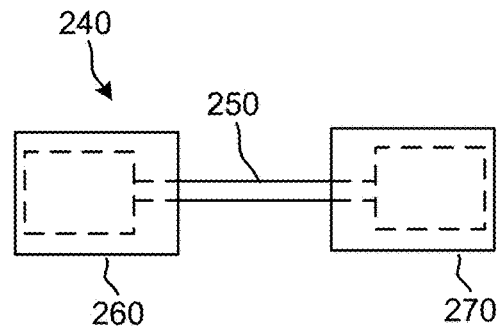
Figure 2C:
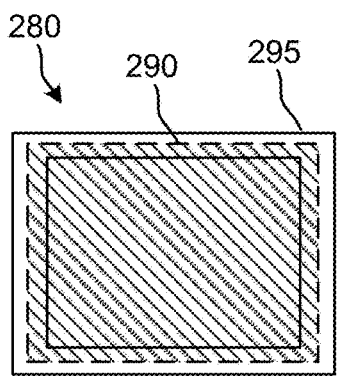
Figure 12:
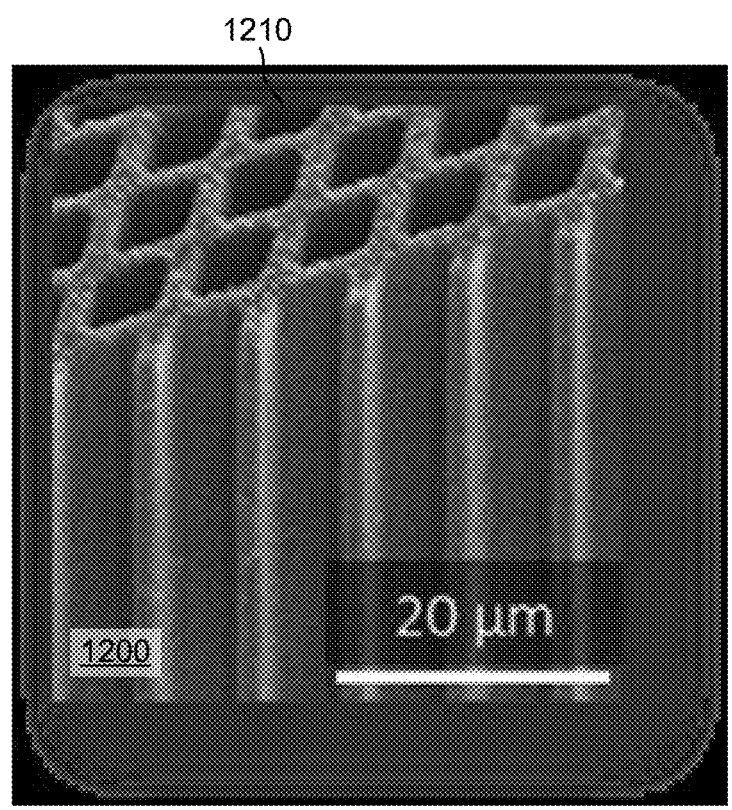
FIG. 12 is an image illustrating a porous, carbon nanotube structure including micro-scale pores defined therein that can be used to form the membrane resonator of FIG. 2C, according to an implementation.

In an implementation, the resonator 110 can be a membrane resonator (e.g., as shown in FIG. 2C) having plurality of micro-scale pores (e.g., pores having diameters on the order of 10 µm) defined therethrough (e.g., as shown in FIG. 12). In other embodiments, resonators having other configurations (e.g., micro-cantilever resonators, micro-beam resonators, etc.) can have such micro-scale pores defined therethrough. Such micro-scale pores can increase flow volume (e.g., of an analyte in gas or liquid phase) through an associated resonator, thus improving sensitivity of a corresponding sensor.

In such implementations, a first micro-scale pore of the plurality of micro-scale pores can be substantially linear and substantially parallel to a second substantially linear micro-scale pore of the plurality of micro-scale pores. In such implementations, a longitudinal axis of the first micro-scale pore can be substantially perpendicular to a direction of vibration of the membrane resonator (e.g., when it is piezoelectrically energized by the piezoelectric actuator 120). Alternatively, the longitudinal axis of the first micro-scale pore can be substantially parallel to a direction of vibration of the membrane resonator (e.g., when it is piezoelectrically energized).

In the sensor 100 shown in FIG. 1, the selective adsorbent (adsorbent) 115 can be selective to (e.g., selectively bind) a corresponding analyte, where the analyte is a chemical compound (e.g., a volatile, a semi-volatile, etc.) or a biologic (e.g., a bio-agent, a micro-organism, etc.). In some implementations, the adsorbent 115 can include, for example, a polymer, a monolayer, an antibody layer, an anion exchange layer, a cation exchange layer, a hydrophobic interaction layer, etc.

The adsorbent 115 can be disposed on an exterior of the resonator 110, where the exterior of the resonator 110 can include surfaces defining the nanoscale pores (which can be a major contributing factor to the increased binding surface area for a fully porous resonator, as compared to a solid material, or mostly solid material resonator). A resonant frequency (a first resonant frequency) of the resonator 110, when piezoelectrically energized by the piezoelectric actuator 120, can be dependent on an amount of the corresponding analyte adsorbed by the adsorbent disposed on the resonator 110. An amount of adsorbed analyte can be determined based on a difference between a second resonant frequency of the resonator 110 that can be determine prior to adsorbing the analyte (e.g., where the second resonant frequency can be referred to as a baseline resonant frequency). A concentration of the analyte (e.g., in a gaseous or aqueous environment to which the resonator 110 was exposed) could then be determined based on the determined amount of the adsorbed analyte. Further to the foregoing examples, depending on the particular implementation, the adsorbent 115 could be a protein, an antibody or a polymer. For instance, proteins and antibodies can be used for biological sensing application, while polymers, such as porous polymers, can be used for chemical sensing applications.

In an implementation of the sensor 100, the resonator 110 can be piezoelectrically coupled with the piezoelectric actuator (actuator) 120, such as described herein. In other implementations, the resonator can be activated using actuation mechanisms other than a piezoelectric actuator. For instance, the actuator 120 can be implemented using a mechanical actuator, a thermal actuator, an acoustic actuator, and so forth.

In the example implementation of FIG. 1, the actuator 120 can be configured to piezoelectrically energize the resonator 110 over a range of frequencies and the detector 130 can be used to determine a resonant frequency of the resonator 110 (e.g., before and/or after exposure to a corresponding analyte). As an example, the detector 130 can include a laser that is configured to direct its light beam onto a vibrating portion of the resonator 110. For example, the laser can be directed at an end (e.g., tip) of a beam of a cantilever resonator, at a center of a beam of a beam resonator, or at a membrane of a membrane resonator. The detector 130 can also include a photo diode that is configured to receive laser light that is reflected from the resonator 110 (e.g., which can vary during oscillation of the resonator 110). Based on the light received at the photo diode, a resonant frequency, as well as a width of a resonant frequency peak (for determining a quality factor Q), can be determined for the resonator 110, such as using various approaches, such as those briefly described herein.

FIGS. 2A through 2C are diagrams that illustrate example sensors 200, 240 and 260, according to implementations. The sensor 200 of FIG. 2A includes a micro-cantilever resonator (resonator) 210 (which can be coated with an appropriate adsorbent, such as those described herein). The sensor 200 can also include an actuator that is used to a clamp (e.g., a base) of the resonator 210. In an implementation, the actuator of the sensor 200 can include a piezoelectric 220 and a metal plate 230 that are piezoelectrically coupled with the resonator 210.

In other implementations, the sensor 200 can include an actuator having other configurations, such as a piezoelectric actuator having a second metal plate 230 that is disposed on top of the piezoelectric 220, creating a stack that includes, from top to bottom, the second metal plate 230, the piezoelectric 220, the base of the resonator 210 and the first metal plate 230. In still other implementations, other actuator configurations are possible, such as mechanical actuators, thermal actuators, acoustic actuators, and so forth, as was previously noted.

The sensor 240 shown in FIG. 2B includes a beam (e.g., a micro-beam) resonator 250, a first clamp 260 and a second clamp 270. As shown (by dashed lines) the ends (e.g., dog-bone shaped ends) of the resonator 250 can be held (clamped), respectively, by the clamp 260 and the clamp 270. In an implementation, one or both of the clamps 260 and 270 can also be an actuator configured to energize (e.g., drive) the resonator 250. For instance, the clamp 260 and/or the clamp 270 can be an actuator having a configuration such as the actuator illustrated in, and described with respect to FIG. 2A. As with the sensor 200, a configuration of the actuator of the sensor 240 can vary depending, for instance, on the particular implementation.

The sensor 280 shown in FIG. 2C includes a membrane (e.g., a micro-scale membrane) resonator 290 and a clamp 295. In FIG. 2C, shading is applied to the resonator 290. As shown (by dashed lines), the edges of the resonator 290 can held (clamped), by the clamp 295. In an implementation, the clamps 295 can be also be an actuator that is configured to energize the resonator 290. For instance, the clamp 295 can be an actuator having a configuration similar to the actuator illustrated in, and described with respect to FIG. 2A.

FIGS. 3A through 3F are images illustrating aspects of a resonant sensor microfabrication process, according to an implementation. The process of FIGS. 3A-3F includes a CNT-M process, such as was briefly discussed above. For purposes of illustration, the process of FIGS. 3A-3F will described with respect to producing the micro-cantilever resonator 210 of FIG. 2A. It will be appreciated, however, that the process illustrated in FIGS. 3A-3F (or similar processes) can be used to produce resonators having other configurations, such as the resonators described herein (e.g., the resonators 250 and 290). It will be further appreciated that the flow rates discussed with respect to FIGS. 3A-3F are given by way of example. In other implementations, other flow rates are possible.

Figure 3A:
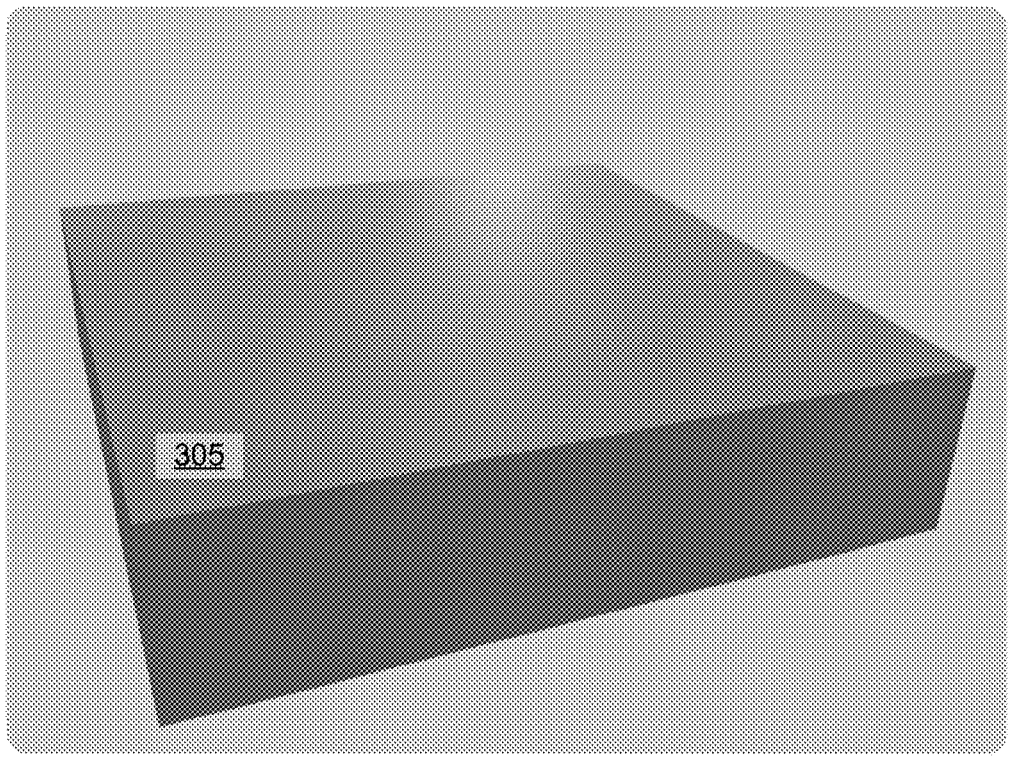
FIGS. 3A through 3F are images illustrating aspects of a resonant sensor microfabrication process, according to an implementation.

In this example implementation of a CNT-M process, as shown in FIG. 3A, a layer of alumina can be deposited on a silicon substrate (substrate) 305. In an implementation, the alumina layer can be approximately 30 nm thick and deposited over an entire surface of the substrate 305 using electron beam evaporation. In other implementations, the alumina layer can have other thicknesses and be deposited using other techniques.

Figure 3B:
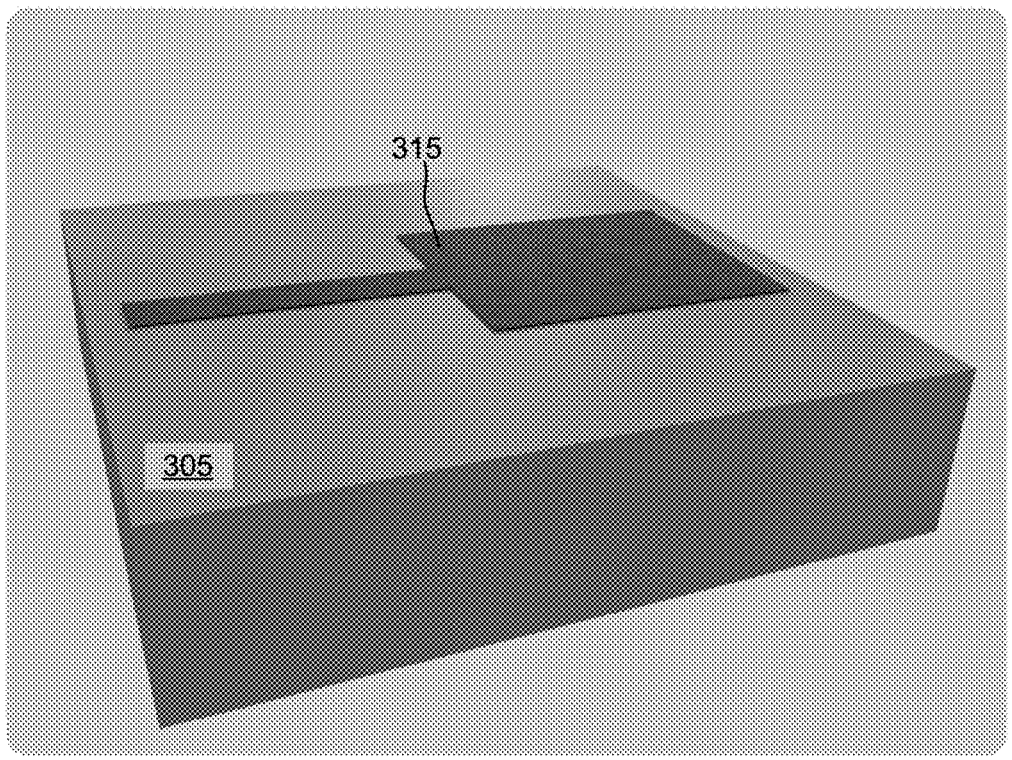

As shown in FIG. 3B, after alumina deposition, a 4 nm thick micro-patterned iron layer 315 can be formed on the alumina coated substrate 305. In an implementation, the iron layer 315 can be formed using, for example, contact photolithography, thermal evaporation and liftoff. The iron layer 315 can act as a catalyst for patterned carbon nanotube growth, while the alumina layer can act as a barrier layer to prevent diffusion of the iron layer 315 into the substrate 305 during thermal processing used to grow carbon nanotubes.

Figure 3C:
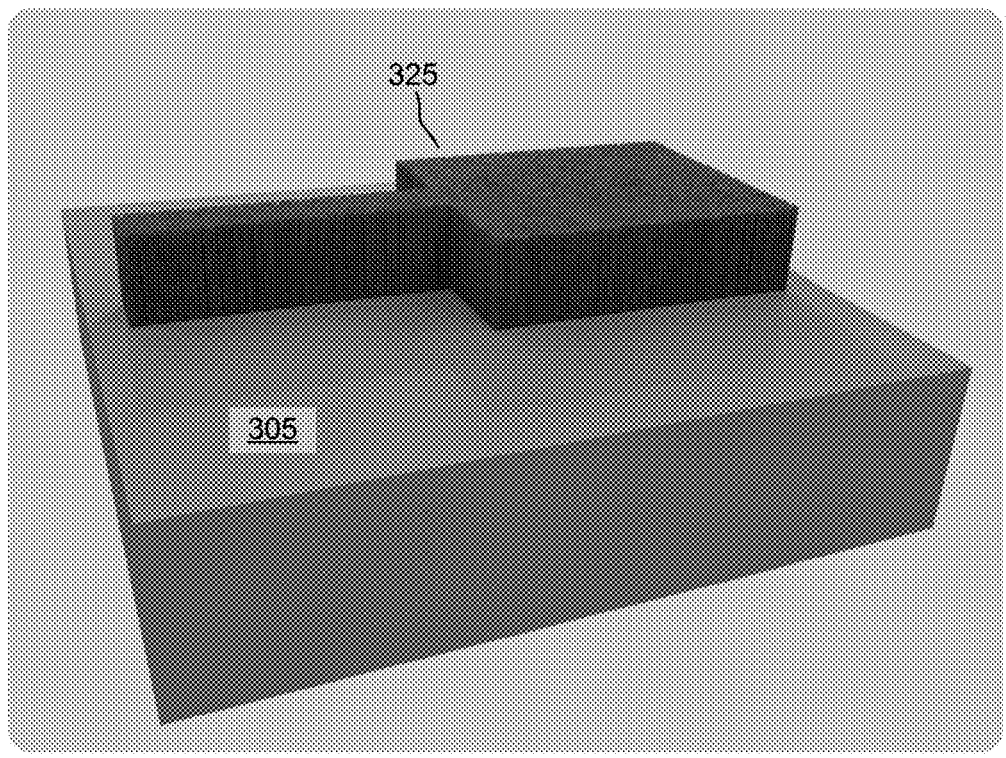
Figure 3D:
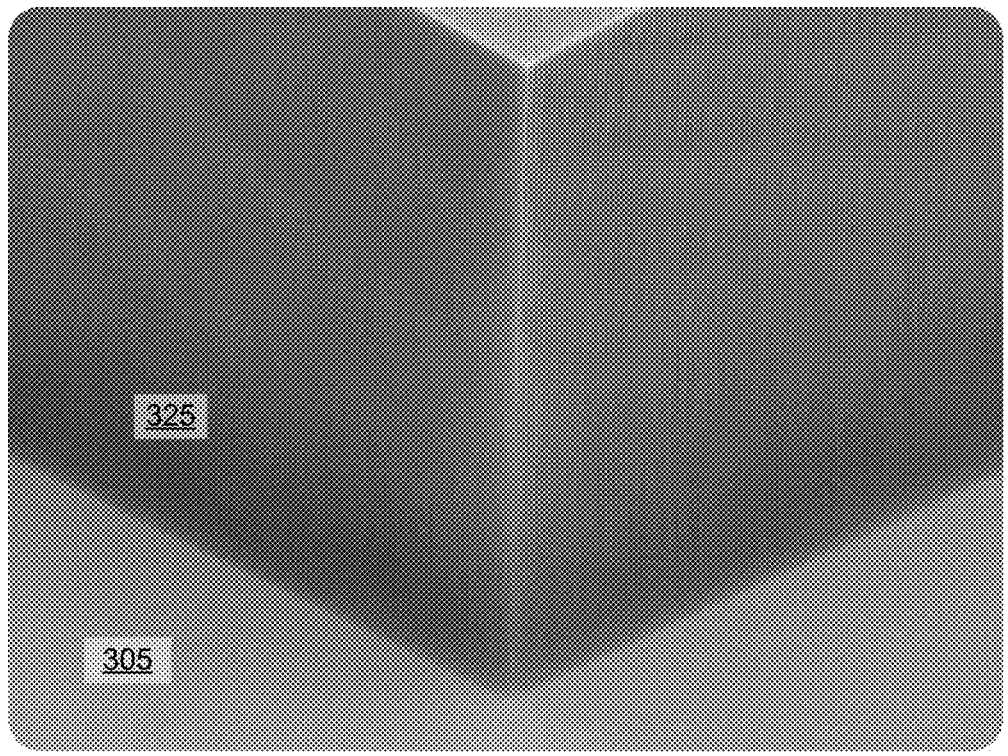

As shown in FIG. 3C, a patterned carbon nanotube forest 325 can be grown from the patterned catalyst iron layer 315. In an implementation, carbon nanotube growth for the carbon nanotube forest 325 can be accomplished as follows. The alumina coated substrate 305 (with the patterned iron layer 315) can be placed into a 1 inch diameter tube furnace with a 230 standard cubic centimeter per minute (sccm) flow of hydrogen gas over the sample as it is heated to a first desired temperature (750 C in one implementation). This hydrogen flow can reduce any oxide that may have formed on the iron layer 315 (and prevent formation of additional oxide). After the temperature of the furnace arrives at the first desired temperature, carbon nanotubes (e.g., substantially vertical carbon nanotubes) can be grown by adding a 230 sccm flow of ethylene gas to the hydrogen flow for a given growth time, where the growth time depends on the desired height (aspect ratio) of the carbon nanotubes of the patterned carbon nanotube forest 325. FIG. 3D is a high resolution image of a portion the patterned carbon nanotube forest 325.

Figure 3E:
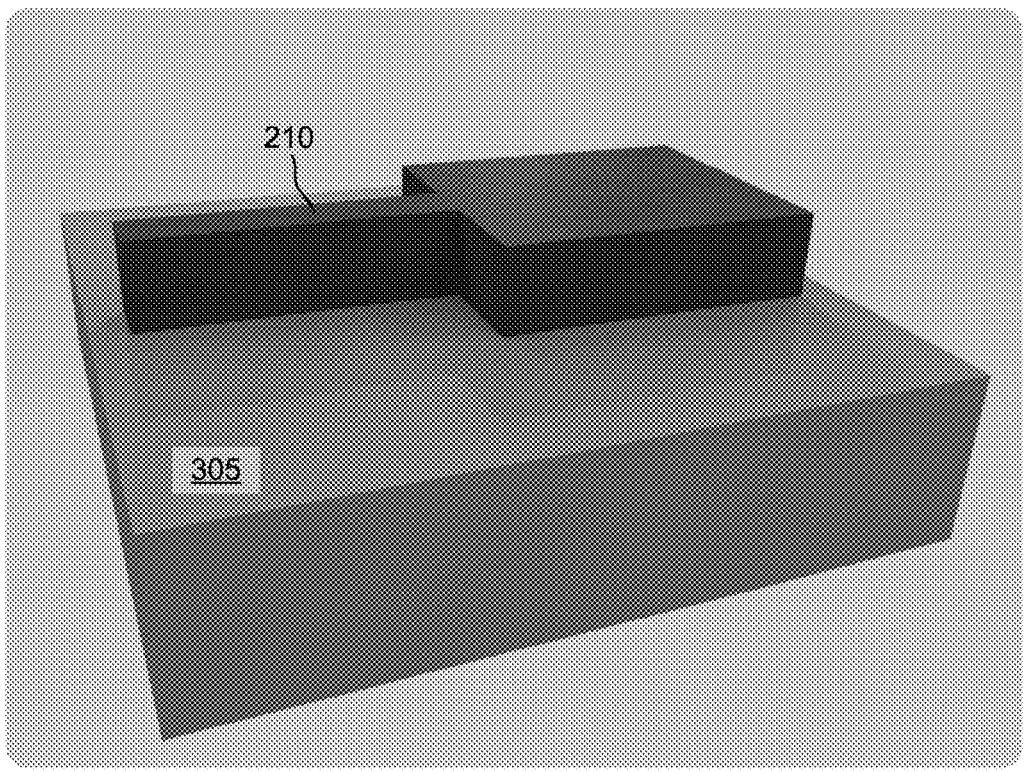
Figure 3F:
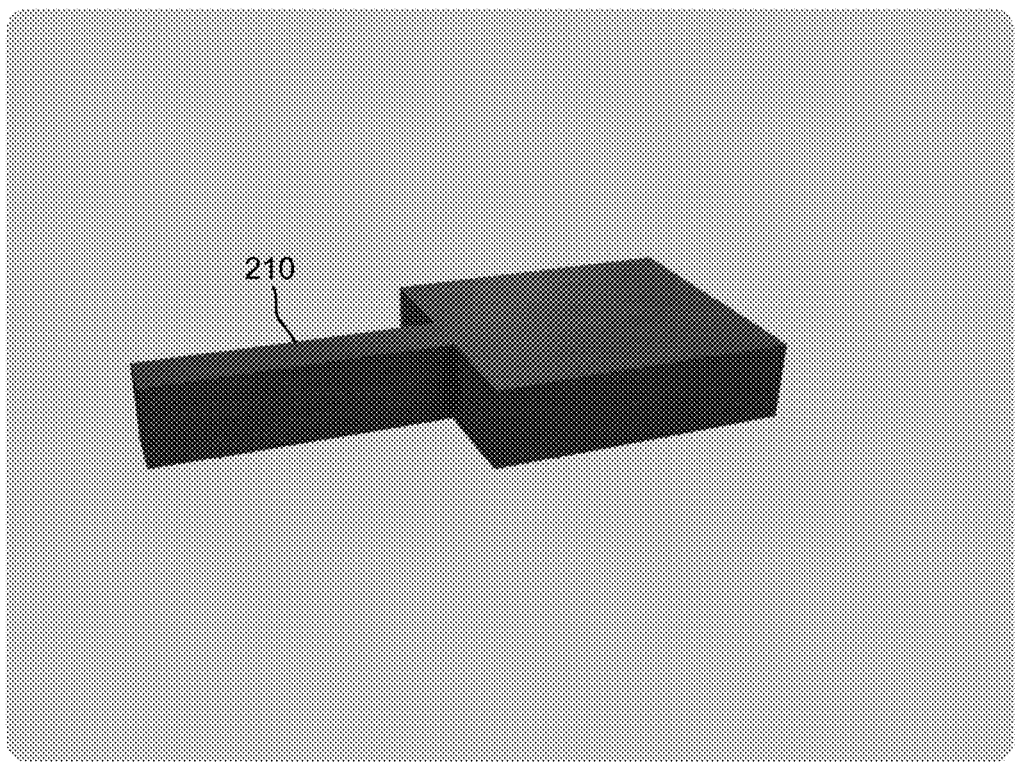

Carbon nanotube growth can then be terminated by replacing the flows of hydrogen and ethylene with an inert gas flow (e.g., an argon flow) to flush the furnace chamber and halt carbon nanotube growth. After establishing the inert gas flow, the furnace temperature can be ramped up to a second (e.g., higher) desired temperature (e.g., 900 C in this example). Once the furnace has reached the second desired temperature, interstices of the carbon nanotubes of the carbon nanotube forest 325 can infiltrated with nanocrystalline carbon, as shown in FIG. 3E, by replacing the inert gas flow with a flow of hydrogen and ethylene (e.g., at the same flow rates previously used for carbon nanotube growth). This infiltration can be used to produce the resonator 210 from the patterned carbon nanotube forest 325 by infiltrating the patterned carbon nanotube forest 325 with a carbon nanofilm. In other implementations, other infiltration materials can be used, such as those described herein.

In this example, the hydrogen and ethylene flow at the second desired temperature can result in, e.g., nanocrystalline carbon infiltration of the carbon nanotube forest 325 (rather than resuming carbon nanotube growth) due to the reduced stability of ethylene at the second desired temperature. At the end of the desired infiltration time, which depends, in part, on a target porosity for the resonator 210, the hydrogen and ethylene gas flows can again be replaced with an inert gas flow (e.g., an argon flow) and the furnace cooled to room temperature.

Once the temperature of the furnace reaches room temperature, the substrate 305 and the resonator 210 can be removed from the furnace and the resonator 210 can be separated from the substrate 305 using mechanical and/or chemical processes. In other implementations, an etching process could be used to release the cantilever beam of the resonator 210 from the substrate 305 while leaving the base of the resonator 210 attached to the substrate 305.

Figure 4A:
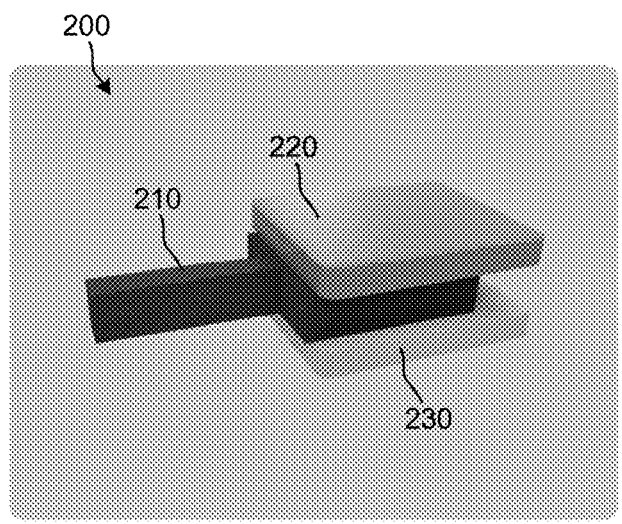
FIGS. 4A through 4C are images illustrating operation of a resonant sensor, according to an implementation.
Figure 4B:
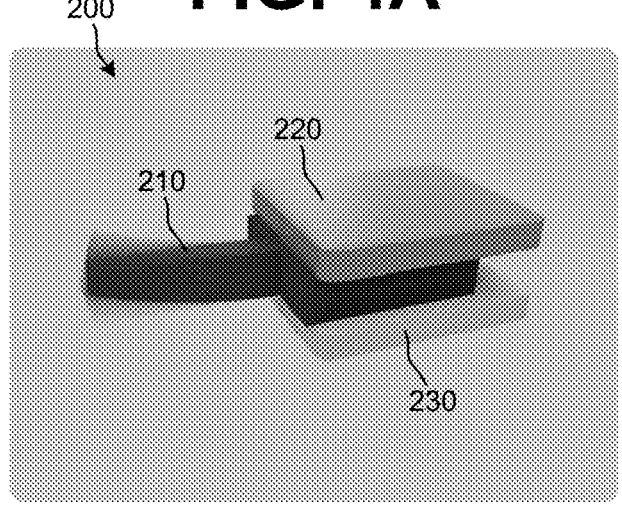
Figure 4C:
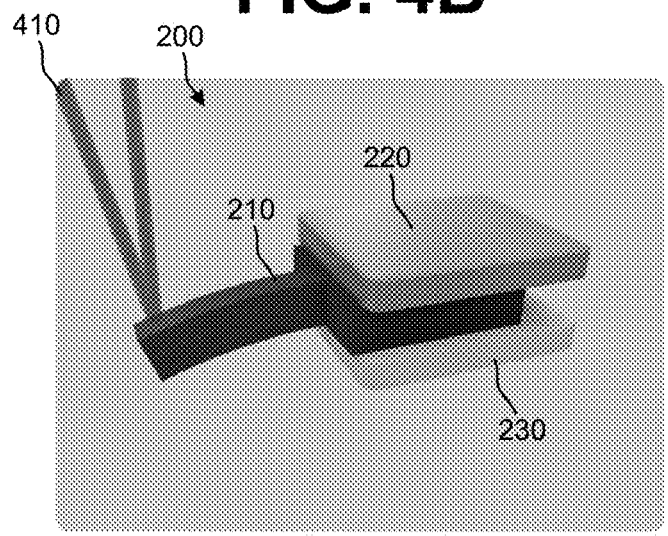

FIGS. 4A through 4C are images illustrating operation of a resonant sensor that includes a porous, monolithic microresonator, according to an implementation. For purposes of clarity and illustration, operation of the sensor 200 is illustrated in FIGS. 4A-4C. In other implementations, similar approaches can be used in conjunction with resonant sensors having other configurations. Further, in still other implementations, other approaches can be used to determine a resonant frequency of a resonant sensor.

FIG. 4A corresponds with FIG. 2A and illustrates the resonator 210 mounted (clamped, piezoelectrically coupled, etc.) in an actuator that includes the piezoelectric 220 and the metal plate 230. The piezoelectric 220 can then be wired to a variable frequency output of a lock-in amplifier, such that oscillations of the resonator 210 can be driven in a controlled manner (e.g., at or near a resonant frequency of the resonator 210), such shown by FIG. 3B.

To determine an amplitude of the cantilever motion of the resonator, such as the motion shown in FIG. 3B, a laser 410 can be directed at the tip of the cantilever beam of the resonator 210, such that the tip reflects a portion of the laser 410's light beam. Such an approach is shown in FIG. 4C. A photodiode (not shown) can then be placed (configured) to receive the reflected beam, with part of the reflected light covering one half of the photodiode face. This arrangement allows the light reflecting from the cantilever to move up and down with the oscillations of the cantilever, such that the photodiode face alternates between receiving no light and full light during each cycle of the cantilever oscillation. The photodiode can be connected, by various methods, to an input of the same lock-in amplifier used to drive the piezoelectric 220 so as to facilitate accurate measurement of cantilever vibration at various frequencies and determine a response of the resonator 210 when it is driven at or near a resonant frequency (e.g., a baseline resonant frequency), such as determining an amplitude of oscillation, changes in oscillation phase, changes in resonant frequency, etc.

To characterize material porosity and nanostructure of the sensor structures described herein, resonator devices were fabricated with a range of infiltration times ranging from 1 to 15 minutes. For each fabricated resonator device, a maximum growth height was measured with a micrometer and the mass of the device was obtained using a microbalance. Because the cross-sectional area of each device can be determined from the design of an associated photolithography mask, the effective density of the entire structure can be computed from these measurements.

The diameter of coated nanotube pillars of these resonator devices can be determined by breaking a sample along a plane parallel to the nanotube growth direction and imaging the exposed coated nanotubes using a scanning electron microscope (SEM). Such fracture planes can be imaged at a bottom, midpoint, top, and side of the nanotube forests to determine coating uniformity. Similar micrographs can also be taken of external sidewalls and the tops of the resonator devices. From each of these images, the diameters of one hundred nanotubes in the focal plane were measured. Nanotube radius was also determined (i.e., as half of the measured diameters).

The area number density of nanotubes in a cross section perpendicular to the growth direction can be measured using different methods. In a first method, cross sections of as fabricated resonator devices are exposed by milling with a focused ion beam (FIB), then imaging via SEM. In a second method, as fabricated resonator devices are first infiltrated with an epoxy resin to reduce redeposition of material into pores before a cross section is exposed by mechanical polishing and imaged by SEM. In a third method, as fabricated resonator devices are first infiltrated with electroplated nickel to reduce redeposition and provide a good conductive path for SEM imaging before a cross section is milled by FIB and imaged with SEM.

FIGS. 5A through 5D are images illustrating microstructure and/or nanostructure of a porous, monolithic resonator, according to implementations. FIG. 5A is an image illustrating a fabricated micro-cantilever resonator 210. FIGS. 5B, 5C and 5D are images showing, respectively, top, side, and cross sectional views illustrating the nanostructure and porosity of the resonator 210. FIG. 5D, specifically, is a FIB milled cross-sectional view of the resonator 210, which provides an indication of the number area density of nanotubes and the corresponding mean distance between nanotubes. Resonator devices, such as the resonator 210, that are milled as fabricated with no additional modification, suffer from extreme redeposition of material during the milling process. This causes the cross section to appear increasingly less porous as the milling process continues. As a result, coated carbon nanotube diameter cannot be estimated using this method. These images can, however, provide an estimate for the number area density of nanotubes, but the depth in the image can make it difficult at times to determine which nanotube segments are intersecting with the cross sectional plane.

Referring again to FIGS. 5A-5D, external device microstructure and nanostructure of the resonator 210 is illustrated. FIG. 5A is an image illustrating a micro-cantilever beam of the resonator 210 extending from a larger base, where the entire resonator 210 is disposed on a silicon substrate. FIG. 5B is an image showing a top face of the resonator 210 and FIG. 5C is an image showing a side wall of the resonator 210. FIG. 5D is an image showing pore sizes and nanotube spacing of a resonator device that was infiltrated for three minutes, where FIG. 5D is specifically a SEM image of a cross section of the corresponding resonator device obtained by milling with a focused ion beam (FIB).

In an attempt to alleviate the problems of redeposition and intersection uncertainty during material characterization, resonator devices can be infiltrated with epoxy prior to cross sectioning. Such epoxy-infiltrated resonator devices are, however, difficult to image by SEM due to charge accumulation, but the resultant mirographs yielded a similar value for the number area density of nanotubes.

A more effective approach to minimizing these characterization measurement issues is to fill the pores of cantilever devices with electroplated nickel before cross sectioning and imaging. Images obtained by this method are very clear and give precise measurements of carbon nanotube number area density. Carbon nanotube number area densities can vary based on the thickness of a catalyst layer that is used, such as the iron layer 315 of FIG. 3B. For instance, carbon nanotube number area densities were measured for nanotubes grown with both a 4 nm and 7 nm thick iron catalyst. For the 4 nm thick iron, the nanotube number area density is measured to be 89-152 nanotubes/$\mu m^2$, while for 7 nm thick iron catalyst it is found to be 70-139 nanotubes/$\mu m^2$. Using a hexagonal packing model, these densities correspond to mean distances between nearest neighbors of 91-128 nm for the 4 nm catalyst case and 91-128 nm for the 7 nm case.

Figure 6:
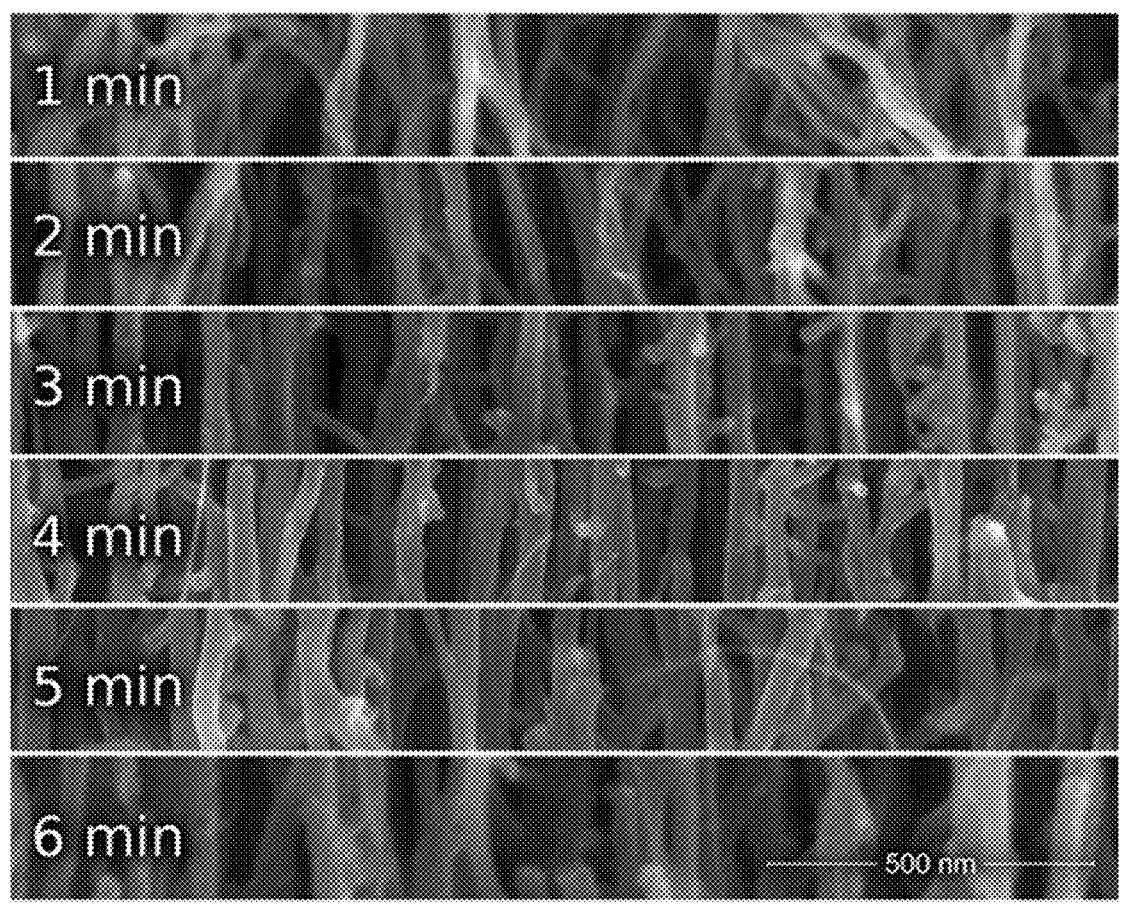
FIG. 6 is a series of images illustrating carbon nanotube diameters that can be included in a porous, monolithic resonant sensor after various time durations of nanocrystalline carbon infiltration on a carbon nanotube forest (infiltration times), according to implementations.

FIG. 6 is a series of images illustrating carbon nanotube diameters that can be included in a porous, monolithic resonant sensor after various time durations of infiltration on a carbon nanotube forest (infiltration times), according to implementations. As shown in FIG. 6, the series of images illustrate nanotubes that been infiltrated (with an infiltration material) from 1 minute to 6 minutes in one minute increments. FIG. 6 shows examples of broken cross sections indicating an increase in the diameter of coated carbon nanotubes with increasing infiltration time. Measurements on these and other similar images are summarized in FIG. 7 described below.

Figure 7:
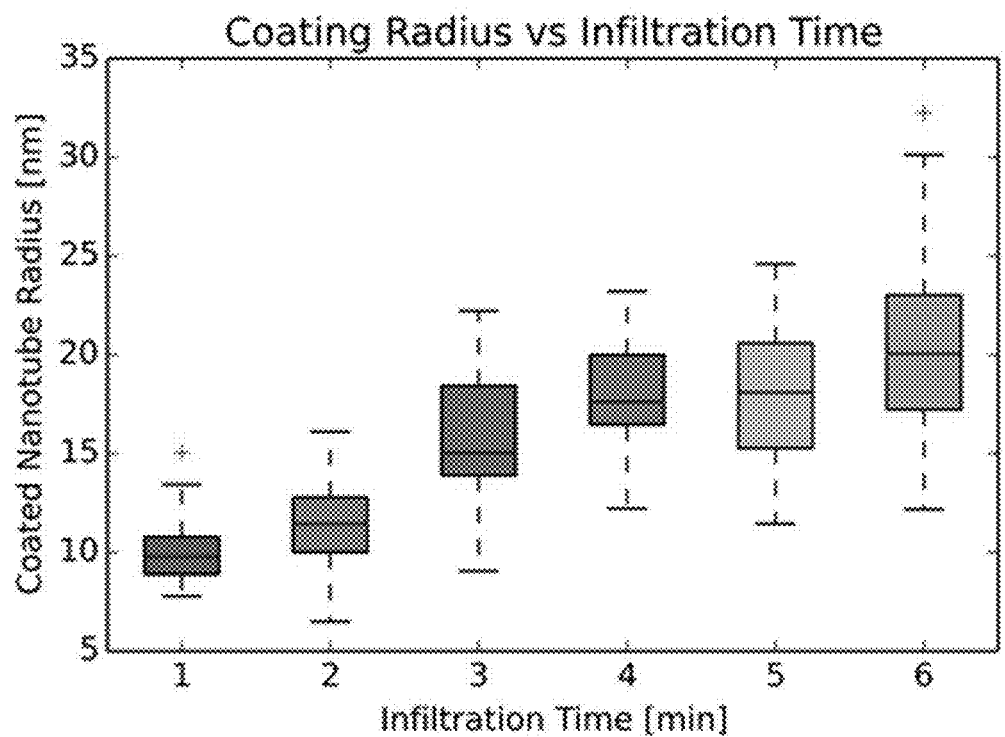
FIG. 7 is a graph illustrating cylindrical radius measurements of coated carbon nanotubes for various infiltration times, according to implementations.

FIG. 7 is a graph illustrating cylindrical radius measurements of coated carbon nanotubes for various infiltration times, according to implementations. In FIG. 7, it can be seen that the mean radius of coated carbon nanotubes increases from approximately 10 nm after 1 minute of infiltration to over 20 nm after 6 minutes of infiltration. This radius continues to increase, following a similar trend at longer infiltration times. However, shorter infiltration times may be of greater interest due to the porosities obtained with shorter infiltration times.

Figure 8:
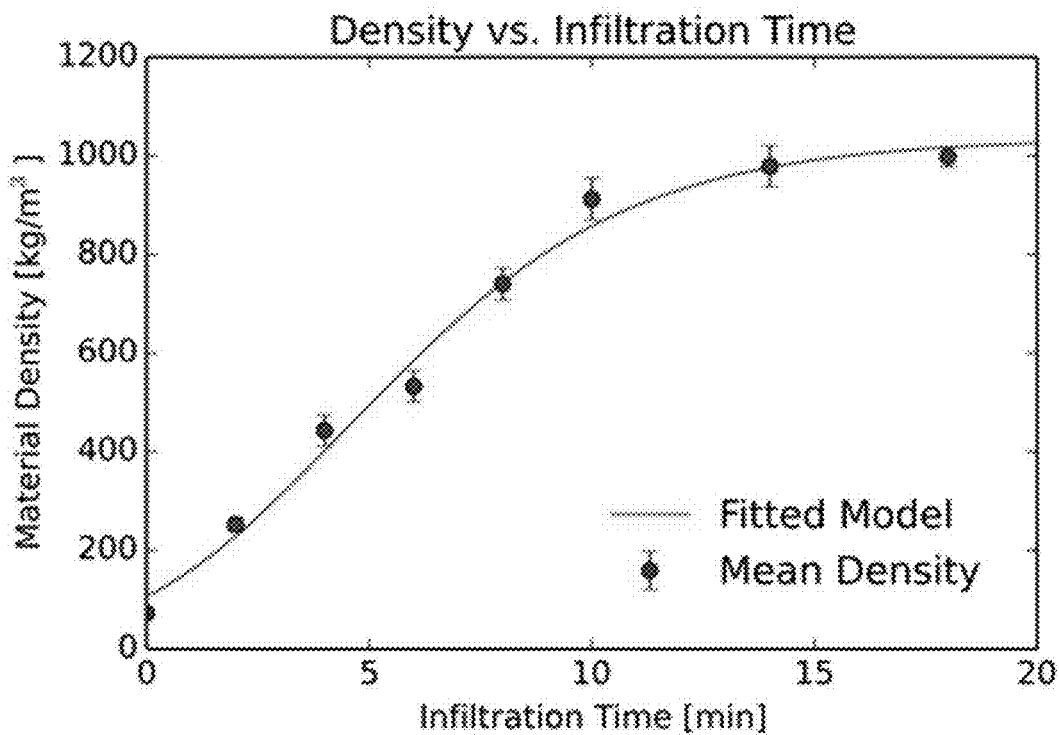
FIG. 8 is a graph illustrating porous, monolithic resonator material density for various infiltration times, according to implementations.

FIG. 8 is a graph illustrating porous, monolithic resonator material density for various infiltration times, according to implementations. In FIG. 8, density data for various infiltration times is shown along with a model of a coating process. Error bars extends below and above the respective means by one standard deviation of the measured data. Specifically, FIG. 8 shows the measurements of the effective density of micro-resonator devices for a range of infiltration times. This data shows that effective resonator density is controllable from below 100 kg/m3 to above 1000 kg/m3. The structures of the illustrated data reach half of an upper density limit after approximately 6 minutes of infiltration. This overall density is an indication of porosity, showing that the fabrication methods can produce cantilevers with porosities that are tunable over a wide range.

The results (data) shown in FIGS. 7 and 8 show good agreement with one another. Effective densities calculated from nanotube number area density and coated nanotube radius are similar to those measured directly for each infiltration time. Micro-cantilevers resonators fabricated with beam lengths ranging from 500 µm to 5 mm, and are found to have fundamental mode resonant frequencies typically between 1 kHz and 100 kHz. Quality factors for these beams are observed to range from approximately 100 up to 1000 when in ambient air.

Figure 9:
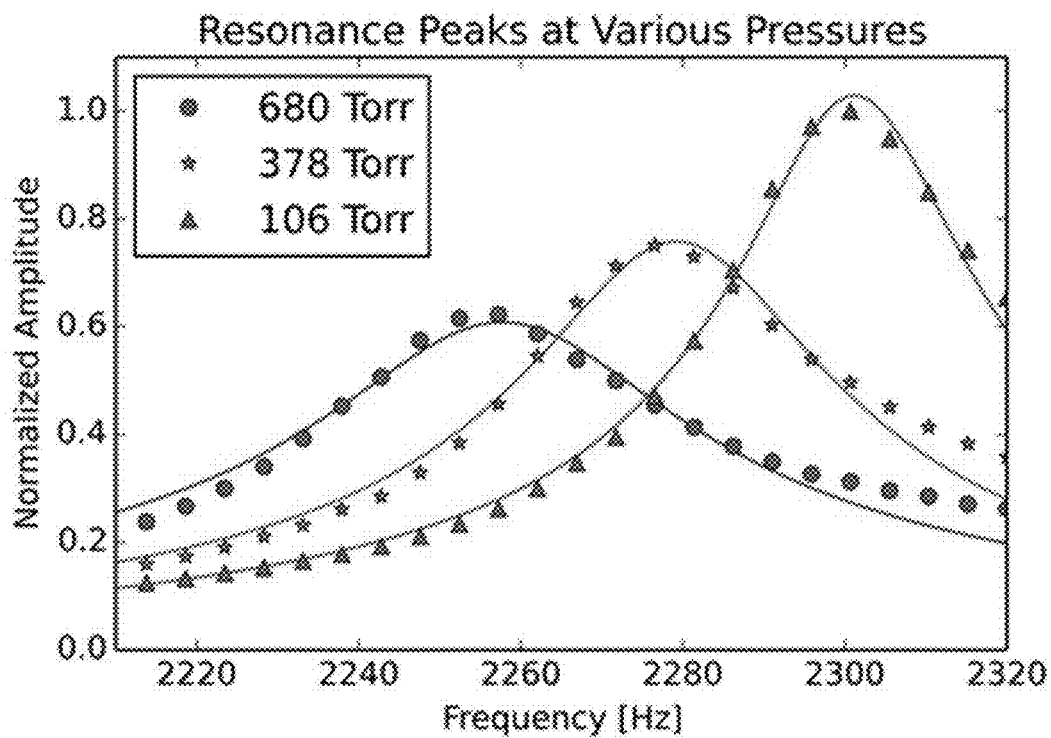
FIG. 9 is a graph illustrating resonance data of a porous, monolithic resonator in a gas environment at various pressures, according to implementations.

FIG. 9 is a graph illustrating resonance data of a porous, monolithic resonator in a gas environment at various pressures, according to implementations. In FIG. 9, resonance data of a single micro-cantilever resonator in a gas environment of three different pressures are shown alongside a model fitted to each case that was used to extract the resonance frequency and quality factor. For the devices corresponding with the data shown in FIG. 9, both the resonant frequencies and the quality factors of the cantilevers were found to vary with the environment gas pressure. An example of the observed resonance peaks at several pressures is also presented in FIG. 9. Of particular interest is the dependence of the quality factor on gas pressure, as it has a more direct impact on sensitivity and also undergoes a much larger percentage change for a given change in pressure than the resonant frequency. The quality factor provides a measure for the total amount of damping in the system.

Figure 10:
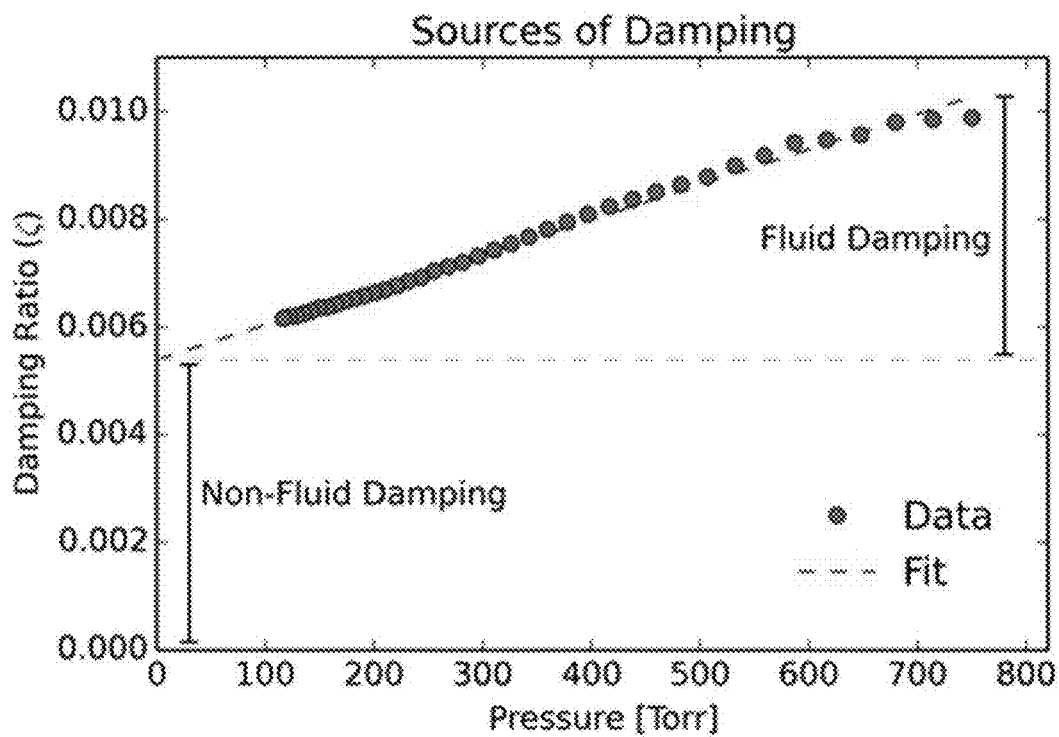
FIG. 10 is a graph illustrating damping ratios for a porous, monolithic resonator in a gas environment at various pressures, according to implementations.

FIG. 10 is a graph illustrating damping ratios for a porous, monolithic resonator in a gas environment at various pressures, according to implementations. In order to discuss damping more directly, a damping ratio $\zeta$ can be computed from the measured quality factor as $\zeta=1/(2Q)$, and can be seen plotted against pressure in FIG. 10. In FIG. 10, the value of a damping ratio ($\zeta=1/(2Q)$) for a given cantilever is shown for a range of environmental gas pressures. It can be seen that at atmospheric pressure approximately half of the total damping is due to fluid damping, the other half being due to clamping and other losses.

From the data shown in FIG. 10, damping ratio appears to follow a linear trend over the range of pressures studied. Fitting a linear model to the damping ratio data and evaluating that model at zero pressure gives an estimate of the amount of damping that comes from sources other than the fluid, such as clamping losses, thermoelastic damping, etc. This allows the determination of a percentage of total damping due to the fluid at any pressure.

Figure 11:
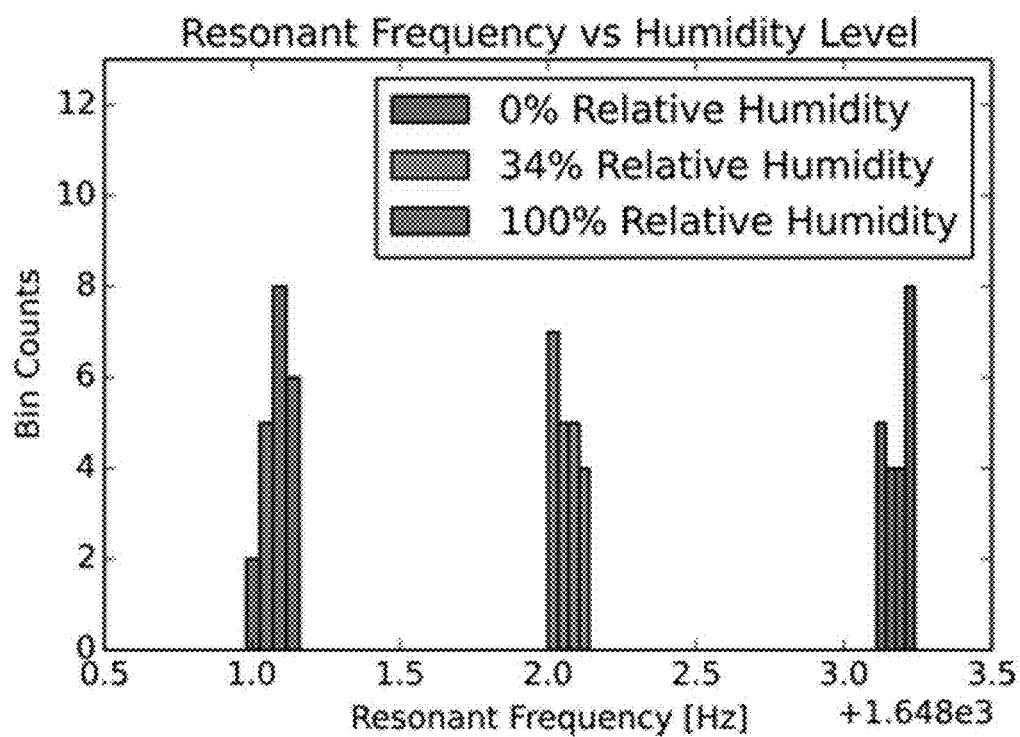
FIG. 11 is a graph illustrating resonant frequency for a porous, monolithic resonator at various relative humidity values, according to implementations.

FIG. 11 is a graph illustrating resonant frequency for a porous, monolithic resonator at various relative humidity values, according to implementations. The data in FIG. 11 is a histogram of resonant frequency for a porous, monolithic resonator at relative humidity values of 0, 34, and 100 percent. This histogram shows observations taken while humidity values were continuously changed in a randomized order.

Specifically, the data of FIG. 11 shows that fluid damping can be as large a contributor as all other sources of damping combined in fluid densities and viscosities equal to or larger than air at atmospheric pressure, and this same trend holds true for the range of cantilever devices studied. It is likely that a large portion of the damping that is not related to the fluid environment in this data could be a result of clamping losses because these cantilevers were removed from the substrate and re-clamped prior to dynamic testing.

To demonstrate operation of micro-cantilever resonators produced using the approaches described herein, the fabricated micro-cantilever resonators were used to measure relative humidity. Note that these cantilevers were hydrophobic as fabricated and were not enhanced with any coating or treatment to increase adsorption of water vapor, so it is expected that sensitivity of these cantilevers to humidity will be much smaller than their sensitivity to other chemicals, especially when adhesion promoting adsorbents (e.g., selective coatings) are applied. Sample results of this humidity sensing study are presented in FIG. 11.

FIG. 12 is an image illustrating a porous, carbon nanotube structure 1200 including micro-scale pores 1210 defined therein and therethrough that can be used to form the resonator structures described herein, according to example implementations. For instance, the micro-scale pores 1210 of the structure 1200 can be defined in a CNT-M process when the catalyst iron layer 315 (FIG. 3B) is patterned. For instance, iron would not be deposited (or would be removed from) the areas where micro-scale pores 1210 are to be defined prior to performing carbon nanotube growth, such as described with respect to FIGS. 3C and 3D.

Using the CNT-M process described herein, porous, monolithic micro-resonators that can be used as resonant chemical and biological sensors can be produced. The porosity of these devices can be controlled by varying an infiltration time of a patterned carbon nanotube forest, e.g., to produce coated carbon nanotubes with diameters adjustable from below 20 nm to well over 40 nm. Because fluid damping can be dominant in sensing environments of interest, thermoelastic damping and other losses are not limiting.

In one general aspect, an apparatus can include a porous, monolithic resonator having nanoscale pores defined therein. The apparatus can also include an actuator coupled with the porous, monolithic resonator. The apparatus can further include a detector operatively associated with the porous, monolithic resonator. The detector can be configured to determine a response of the resonator when the resonator is driven at or near a resonant frequency of the porous, monolithic resonator by the actuator.

Implementations can include one or more of the following features. For example, the porous, monolithic resonator can include a carbon nanotube composite structure including a patterned carbon nanotube forest and an infiltration material. At least a portion of the patterned carbon nanotube forest can have a height:width aspect ratio up to 200:1, up to 300:1 or up to 500:1. The porous, monolithic resonator can be one of a cantilever resonator, a beam resonator and a membrane resonator.

The porous, monolithic resonator can include a plurality of micro-scale pores defined therethrough, a first micro-scale pore of the plurality of micro-scale pores being substantially linear and substantially parallel to a second substantially linear micro-scale pore of the plurality of micro-scale pores. A longitudinal axis of the first micro-scale pore can be substantially perpendicular to a direction of vibration of the porous, monolithic resonator. A longitudinal axis of the first micro-scale pore can be substantially parallel to a direction of vibration of the porous, monolithic resonator.

The apparatus can include an adsorbent that is selective to a corresponding analyte, the adsorbent being disposed on an exterior of the porous, monolithic resonator. A resonant frequency of the porous, monolithic resonator can be dependent on an amount of the corresponding analyte adsorbed by the adsorbent. The exterior of the porous, monolithic resonator can include surfaces defining the nanoscale pores. The adsorbent can be one of a protein, an antibody and a polymer.

In another general aspect, a method can include defining a porous, monolithic resonator having nanoscale pores defined therein. The method can also include depositing an adsorbent that is selective to a corresponding analyte on an exterior of the porous, monolithic resonator. The exterior of the porous, monolithic resonator can include surfaces defining the nanoscale pores.

Implementations can include one or more of the following features. For example, the method can include coupling the porous, monolithic resonator with an actuator; exposing at least a portion of the porous, monolithic resonator to the corresponding analyte; energizing the porous, monolithic resonator with the actuator at or around a resonant frequency of the porous, monolithic resonator; determining a response of the porous, monolithic resonator to the energizing, the response being one of a phase shift, and an amplitude change and a change in the resonant frequency; and determining, based on the response, an amount of the analyte adsorbed by the adsorbent.

The resonant frequency can be a first resonant frequency. The method can include, prior to exposing the at least a portion of the porous, monolithic resonator to the corresponding analyte: energizing the porous, monolithic resonator with the actuator; determining a second resonant frequency of the porous, monolithic resonator; and de-energizing the porous, monolithic resonator. The determining the amount of the analyte adsorbed by the adsorbent can be based on a difference between the second resonant frequency and the first resonant frequency.

The exposing the at least a portion of the porous, monolithic resonator to the corresponding analyte can include exposing the at least a portion of the porous, monolithic resonator to the corresponding analyte in a gas phase. The exposing the at least a portion of the porous, monolithic resonator to the corresponding analyte can include exposing the at least a portion of the porous, monolithic resonator to the corresponding analyte in a liquid phase.

In another general aspect, an apparatus can include a porous, monolithic resonator having nanoscale pores defined therein. The apparatus can also include an adsorbent selective to a given analyte disposed on an exterior of the porous, monolithic resonator. The exterior of the porous, monolithic resonator can include surfaces defining the nanoscale pores.

Implementations can include one or more of the following features. For example, the porous, monolithic resonator can have a quality factor of at least 100 in a gas environment. The porous, monolithic resonator can have a quality factor of at least 10 in an aqueous environment. The adsorbent can be one of a protein, an antibody and a polymer. The adsorbent can be a porous polymer configured to adsorb at least one of a volatile and a semi-volatile chemical compound. The porous, monolithic resonator can include a patterned carbon nanotube structure including a carbon nanotube forest infiltrated with an infiltration material.

It will understood that, in the foregoing disclosure, when an element, such as a layer, a region, or a substrate, is referred to as being on, connected to, electrically connected to, coupled to, or electrically coupled to another element, it may be directly on, connected or coupled to the other element, or one or more intervening elements may be present. In contrast, when an element is referred to as being directly on, directly connected to or directly coupled to another element or layer, there are no intervening elements or layers present. Although the terms directly on, directly connected to, or directly coupled to may not be used throughout the detailed description, elements that are shown as being directly on, directly connected or directly coupled can be referred to as such. The claims of the application may be amended to recite exemplary relationships described in the specification or shown in the figures.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. An apparatus, comprising:
   a porous, monolithic resonator having nanoscale pores disposed therein, the porous, monolithic resonator including a carbon nanotube composite structure, the carbon nanotube composite structure including a patterned carbon nanotube forest and an infiltration material, the infiltration material partially filling interstices between carbon nanotubes of the patterned carbon nanotube forest;
   an actuator coupled with the porous, monolithic resonator; and
   a detector operatively associated with the porous, monolithic resonator, the detector being configured to determine a response of the porous, monolithic resonator when the porous, monolithic resonator is driven at or near a resonant frequency of the porous, monolithic resonator by the actuator.

2. The apparatus of claim 1, at least a portion of the patterned carbon nanotube forest has a height: width aspect ratio up to 200:1, up to 300:1 or up to 500:1.

3. The apparatus of claim 1, wherein the porous, monolithic resonator is one of a cantilever resonator, a beam resonator and a membrane resonator.

4. The apparatus of claim 1, wherein the porous, monolithic resonator includes a plurality of patterned micro-scale pores defined therethrough, a first micro-scale pore of the plurality of patterned micro-scale pores being substantially linear and substantially parallel to a second substantially linear micro-scale pore of the plurality of patterned micro-scale pores.

5. The apparatus of claim 4, wherein a longitudinal axis of the first micro-scale pore is substantially perpendicular to a direction of vibration of the porous, monolithic resonator.

6. The apparatus of claim 4, wherein a longitudinal axis of the first micro-scale pore is substantially parallel to a direction of vibration of the porous, monolithic resonator.

7. The apparatus of claim 1, further comprising an adsorbent that is selective to a corresponding analyte disposed on an exterior of the porous, monolithic resonator, a resonant frequency of the porous, monolithic resonator being dependent on an amount of the corresponding analyte adsorbed by the adsorbent, the exterior of the porous, monolithic resonator including surfaces defining the nanoscale pores.

8. The apparatus of claim 7, wherein the adsorbent is one of a protein, an antibody and a polymer.

9. The apparatus of claim 1, wherein the porous, monolithic resonator has a quality factor of at least 100 in a gas environment.

10. The apparatus of claim 1, wherein the porous, monolithic resonator has a quality factor of at least 10 in an aqueous environment.

11. The apparatus of claim 7, wherein the adsorbent is a porous polymer configured to adsorb at least one of a volatile or a semi-volatile chemical compound.

12. A method, comprising:
    defining a porous, monolithic resonator having nanoscale pores defined therein, the porous, monolithic resonator including a carbon nanotube composite structure, the carbon nanotube composite structure including a patterned carbon nanotube forest and an infiltration material, the infiltration material partially filling interstices between carbon nanotubes of the patterned carbon nanotube forest;
    coupling an actuator with the porous, monolithic resonator;
    operatively associating a detector with the porous, monolithic resonator; and
    determining a response of the porous, monolithic resonator when the porous, monolithic resonator is driven at or near a resonant frequency of the porous, monolithic resonator by the actuator.

13. The method of claim 12, further comprising:
    prior to operatively associating the detector with the porous, monolithic resonator:
        depositing an adsorbent that is selective to a corresponding analyte on an exterior of the porous, monolithic resonator; and
        exposing at least a portion of the porous, monolithic resonator to the corresponding analyte,
    wherein determining the response of the porous, monolithic resonator includes:
        energizing the porous, monolithic resonator with the actuator at or around the resonant frequency of the porous, monolithic resonator, the response being one of a phase shift, and an amplitude change and a change in the resonant frequency; and
        determining, based on the response, an amount of the corresponding analyte adsorbed by the adsorbent.

14. The method of claim 13, wherein the resonant frequency is a first resonant frequency, the method further comprising, prior to exposing the at least a portion of the porous, monolithic resonator to the corresponding analyte:
    energizing the porous, monolithic resonator with the actuator;
    determining a second resonant frequency of the porous, monolithic resonator; and
    de-energizing the porous, monolithic resonator, the determining the amount of the corresponding analyte adsorbed by the adsorbent is based on a difference between the second resonant frequency and the first resonant frequency.

15. The method of claim 13, wherein the exposing the at least a portion of the porous, monolithic resonator to the corresponding analyte includes exposing the at least a portion of the porous, monolithic resonator to the corresponding analyte in a gas phase.

16. The method of claim 13, wherein the exposing the at least a portion of the porous, monolithic resonator to the corresponding analyte includes exposing the at least a portion of the porous, monolithic resonator to the corresponding analyte in a liquid phase.

17. The method of claim 13, wherein the adsorbent is one of a protein, an antibody and a polymer.

* * * * *